United States Patent
Eriksson (10) Patent No.: US 10,549,120 B2
(45) Date of Patent: Feb. 4, 2020

(54) METHOD, A COMPUTER PROGRAM PRODUCT AND A COMPUTER SYSTEM FOR RADIOTHERAPY OPTIMIZATION

(71) Applicant: RaySearch Laboratories AB, Stockholm (SE)

(72) Inventor: Kjell Eriksson, Bålsta (SE)

(73) Assignee: RaySearch Laboratories AB, Stockholm (SE)

(*) Notice: Subject to any disclaimer, the term of this patent is extended or adjusted under 35 U.S.C. 154(b) by 0 days.

(21) Appl. No.: 15/580,765

(22) PCT Filed: Jun. 9, 2016

(86) PCT No.: PCT/EP2016/063163
§ 371 (c)(1),
(2) Date: Dec. 8, 2017

(87) PCT Pub. No.: WO2016/198525
PCT Pub. Date: Dec. 15, 2016

(65) Prior Publication Data
US 2018/0221685 A1    Aug. 9, 2018

(30) Foreign Application Priority Data

Jun. 12, 2015 (EP) .................................... 15171833

(51) Int. Cl.
*A61N 5/10* (2006.01)
*G16H 50/20* (2018.01)
*G06F 19/00* (2018.01)

(52) U.S. Cl.
CPC ............ *A61N 5/1036* (2013.01); *G16H 50/20* (2018.01); *G06F 19/3481* (2013.01)

(58) Field of Classification Search
CPC .... A61N 5/103; A61N 5/1031; A61N 5/1036; A61N 5/1042; A61N 5/1045
See application file for complete search history.

(56) References Cited

U.S. PATENT DOCUMENTS

| | | | |
|---|---|---|---|
| 2004/0190680 A1* | 9/2004 | Chang | A61N 5/1042 378/65 |
| 2005/0111621 A1* | 5/2005 | Riker | A61N 5/1031 378/65 |
| 2006/0045238 A1 | 3/2006 | Nguyen | |
| 2008/0298550 A1 | 12/2008 | Otto | |
| 2012/0065489 A1 | 3/2012 | Nord et al. | |
| 2013/0187062 A1 | 7/2013 | Nord et al. | |
| 2013/0304503 A1 | 11/2013 | Kuefer et al. | |

* cited by examiner

*Primary Examiner* — Carrie R Dorna
(74) *Attorney, Agent, or Firm* — Drinker Biddle & Reath LLP (57) ABSTRACT

An interpolation of deliverable radiotherapy treatment plans is facilitated by restricting the movement of the multi-leaf collimator leaves between optimization steps.

12 Claims, 5 Drawing Sheets

METHOD, A COMPUTER PROGRAM PRODUCT AND A COMPUTER SYSTEM FOR RADIOTHERAPY OPTIMIZATION

This application is the National Stage of International Application No. PCT/EP2016/063163, filed Jun. 9, 2016, and claims benefit of European Patent Application No. 15171833.5, filed Jun. 12, 2015, the entire contents of which are incorporated by reference herein.

TECHNICAL FIELD

The present invention relates to the optimization of radiotherapy treatment plans, in particular for radiotherapy techniques in which a multi-leaf collimator (MLC) is used.

BACKGROUND AND RELATED ART

Radiotherapy treatment involves subjecting a patient to a type of radiation, which is normally distributed over a number of beams delivered to the patient. A radiotherapy treatment plan contains a number of beam properties that specify the beam setup to be used when each beam of the plan is delivered to the patient. The beam properties depend on the treatment technique and include for example gantry angle, the leaf positions of the multi-leaf collimator (MLC), the jaw positions and the machine output in monitor units (MU). For intensity modulated treatment techniques, e.g. VMAT, SMLC and DMLC, as well as conformal arcs, each beam is divided into a number of control points or segments. For each control point or segment the machine output in MU (or the segment weight), the jaw positions and the MLC leaf positions are specified, together with other properties such as gantry and collimator angles. Other techniques involving the use of an MLC include 3DCRT and static arcs.

Treatment plans can be created in many different ways, well known to the person skilled in the art, including forward planning and inverse planning. In forward planning, the beam setups are set manually by for example drawing the MLC shape or based on geometrical projections. In inverse planning methods, the beam setups are the result of a treatment plan optimization that aims to fulfil specified requirements on the dose distribution. Inverse planning may be performed on the fluence map or on the machine parameters. In fluence map optimization, ideal fluence profiles are optimized to achieve the optimal dose distribution with respect to the objective function used. After the optimization the ideal fluence maps are converted into deliverable beam setups including jaw positions, MLC-positions and the MU of each control point (or segment). The conversion step usually introduces a deterioration of the dose distribution compared to the dose distribution of the ideal fluence profile. In direct machine parameter optimization the beam settings, such as the MLC positions and MU of each control point (or segment), are directly optimized and the resulting beam setups are deliverable. In this case there is no need for a conversion step. Therefore, direct machine parameter optimization has proven to improve treatment plan quality substantially for most treatment techniques. The present invention is mainly related to inverse planning, but can also be applied on any other planning technique such as forward planning.

In inverse planning it is difficult to know beforehand what the effect of modifying the optimization problem will be. If a plan is created and for example the maximum dose to an organ at risk is too high, it might be a good idea to try to decrease the maximum dose level or increase the weight of the objective function defined on that organ or structure and restart the optimization. It is not unusual that the dose according to the resulting plan will be reduced beyond what was intended and/or that the dose to some other structures like the tumor and some other organs at risk have become unacceptable due to conflicting objectives. Interpolation between the two plans enables real time navigation so that the best trade-off between the two plans can be achieved.

Common for the plan generation techniques is that a dose distribution is computed from the obtained beam settings and evaluated to determine the quality of the dose distribution. Independent of plan generation technique a fluence profile can be computed from the beam settings and stored as an intermediate step in the dose computation.

It is possible to create two or more alternative treatment plans with different priorities on the clinical goals using any of the planning techniques. In some cases, none of the plans generated in this way are quite satisfactory. In such situations it would be beneficial to interpolate between treatment plans. The goal of treatment plan interpolation is to interpolate the deliverable beam parameters of at least two treatment plans in such a way that the resulting dose distribution is approximately an interpolation of the dose distributions of the plans. This enables the exploration of conflicting objectives in what is experienced as real time. By controlling the interpolation weights it is possible to navigate in a combination of the generated plans to find the best trade-off between the conflicting goals.

The navigation can be performed in many different ways, e.g. using textboxes, sliders, or pushing the DVH curves, and the resulting dose distribution is constantly updated when the weights are updated. Systems are available in which the interpolation weight can be controlled using a text box or a slider and the result can be displayed in what is experienced as real time. Such systems are commercially available, for example the Multi Criteria Optimization function in applicant's RayStation systems.

For the interpolation to work properly it is important that the interpolation of the treatment beams of the different plans at least approximately generates a dose distribution that is an interpolation between the dose distributions of the different plans. Interpolation between radiotherapy treatment plans is fairly straightforward if the beams are represented as fluence profiles, because of the linear relationship between the fluence and the dose. An interpolation between the fluences of the plans followed by a dose calculation from the interpolated fluence gives the same dose distribution that would be the result from interpolating the dose distributions of the plans directly. However, interpolating fluence profiles requires a second step, where the resulting interpolated fluence profiles are converted to deliverable beam setups and the final dose is recalculated. This conversion step takes time and introduces deviations from the interpolated ideal dose distribution.

It would therefore be desirable to interpolate directly in the deliverable beam setups, since the actual result will then be visible immediately and the conversion step is not needed. However, attempts to interpolate between deliverable plans have proven difficult because the parameters of the deliverable beam setups are not linearly related to the fluence. Interpolating between the control points of two deliverable plans will in most situations not result in an interpolation between the two dose distributions.

US 2013/0304503 discloses an optimization method, which allows local optimization of a small part of a deliverable plan based on a small change in the dose distribution. In such cases, an interpolation between the initial and the optimized plan will often produce a result that can be used for deliverable plan interpolation. This method only works when the change to the dose in each optimization step is small enough, or the volume where the dose is changed is small enough.

It would be beneficial to be able to interpolate directly deliverable plans with significant differences between the dose distributions to enable navigation between substantial clinical goal trade-offs.

SUMMARY OF THE INVENTION

It is therefore an object of the invention to facilitate interpolation between different deliverable plans without restrictions to the dose or to the volume where the dose is changed.

The invention relates to a method of creating an interpolated radiotherapy treatment plan, comprising the following steps:
providing a first deliverable treatment plan,
providing a second deliverable treatment plan,
said first and second treatment plans comprising at least one of the following:
position settings for a number of leaves of a multi-leaf collimator
position settings for the jaws
wherein at least one of the following constraints is applied:
a maximum difference in position settings for the leaves between the first and the second treatment plan,
a maximum difference in jaw positions between the first and the second treatment plan, and
creating an interpolated treatment plan based on the first and the second treatment plans.

The method according to the invention enables interpolation between two or more deliverable plans. Because of the constraint on how much the control points may differ between the plans, the risk of unwanted effects which may occur when interpolating between deliverable plans is practically eliminated. The invention therefore enables interpolation between deliverable plans with a good quality result. Interpolating between deliverable plans instead of between ideal fluence-based plans means that there is no need for a conversion of the fluence profile to a deliverable plan. This conversion step causes a deterioration of the dose distribution and takes time to perform. According to the invention, after each interpolation the dose is recalculated, and with a fast dose computation, the interpolation can be performed in what is experienced as real time and the result can be visible immediately since the resulting plan is already a deliverable plan. Because the computed dose distribution will be approximately the same as an interpolation between the dose distributions of the interpolated plans, the interpolated dose distribution can be displayed while waiting for the actual dose computation to finish.

Hence, the method according to the invention saves time and increases the quality of the treatment plan by avoiding the conversion step that is required after interpolation between fluence based treatment plans.

Because of the limit on how much the collimator leaf positions, and optionally the jaw positions, may vary between the plans, no restriction has to be set for the changes in dose during optimization. The dose distributions is allowed to vary as much as necessary to be able to improve the different objectives of the two plans as much as possible, given that the leaf position constraints between the plans are fulfilled.

According to a first embodiment, the first and the second treatment plans are optimized simultaneously using a first and a second optimization problem, respectively. It is also possible to provide three or more deliverable treatment plans and to optimize all of the plans simultaneously using different optimization problems. In this case, the same constraints should apply between all the treatment plans. The interpolated deliverable plan is obtained by interpolation between any two of the plans, or between more plans at the same time.

According to a second, alternative embodiment, the second deliverable treatment plan is created based on the first deliverable treatment plan. In this case, it is possible to create a sequence of plans, by creating a fourth deliverable treatment plan based on the second deliverable treatment plan, etc. In this case, the constraints should apply between the first and the second treatment plan, and between the second and the fourth treatment plan, respectively. This means that by creating a sequence of plans the MLC leaf and jaw settings of the fourth, or later, treatment plan may differ more from those of the first treatment plan than what is allowed by the constraints. The interpolated treatment plan may be based on interpolation between any pair of treatment plans where one was based on the other. In this embodiment the first treatment plan should preferably have a different optimization problem from that of the subsequent plans. The subsequent plans may be based on the same or different optimization problems.

Alternatively, based on the second embodiment above, a number of subsequent treatment plans may be created based on the first treatment plan, applying the constraint between the first plan and each of the subsequent treatment plans. In this case the interpolated treatment plan may be obtained based on at interpolation between either the first and the second treatment plan, or between the first and any of the other treatment plans. It is also possible to interpolate between any combination of more than two treatment plans simultaneously. In this embodiment, preferably all treatment plans created based on the first treatment plan are based on different optimization problems.

The optimization problems may comprise, for example, reducing the dose to at least one organ at risk, maintaining a uniform high dose to a target, and/or reducing the delivery time.

Preferably the limit corresponds substantially to the resolution of the fluence map. Suitable values have been found to be between 0.0 cm and 2.0 cm, or preferably between 0.5 and 1.5 cm, for example 0.5 cm, 1 cm or 1.5 cm, which still allows significant differences in the dose distributions of the optimized plans.

The method according to the invention has been developed for deliverable segmented mode (SMLC) plans, but will also work for all treatment techniques where an MLC is used such as volumetric modulated arc therapy (VMAT), dynamic mode (DMLC), 3D-CRT, conformal arcs.

As is common in the art, the invention is implemented in a computer program product comprising computer readable code means which, when run in a computer will cause the computer to perform the method according to any above embodiments. The computer program product is typically stored on a carrier, such as a hard disc or any other type of suitable carrier.

The invention also relates to a computer system for performing dose calculations for radiotherapy according to the invention. The system comprises processing means for performing registration of images, and includes a memory unit having stored therein a computer program product according to the above, in such a way that the computer program product, when executed, will control the processing means to perform the inventive method.

BRIEF DESCRIPTION OF THE DRAWINGS

The invention will be described in more detail in the following, with reference to the appended drawings, in which.

DETAILED DESCRIPTION OF PREFERRED EMBODIMENTS

Figure 1A:
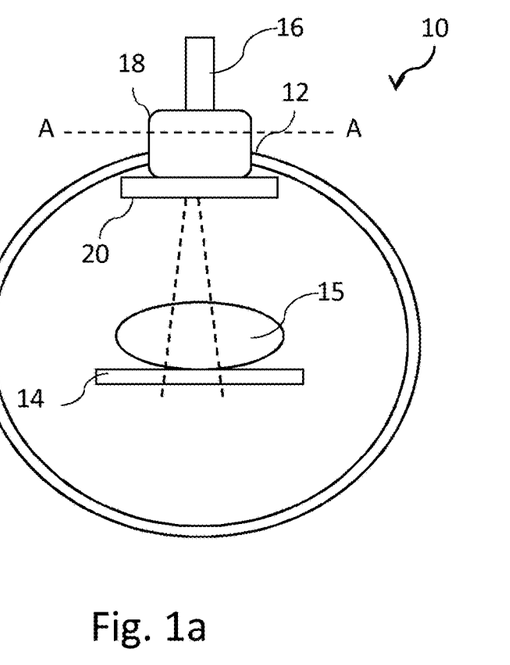
FIG. 1a illustrates a system for delivery of radiotherapy treatment to a patient and FIG. 1b illustrates the setting of the leaves of an MLC.

FIG. 1a illustrates schematically a radiotherapy system 10 as is common in the art. The system comprises a rotatable gantry 12 having a radiation source 16 for providing therapeutic radiation to a patient 15 situated on a patient support 14. Between the gantry 12 and the patient 15, beam shaping devices are positioned, including a multi-leaf collimator (MLC) 18. Typically also a set of moveable blocks referred to as jaws 20 are positioned above or below the MLC 18, to block substantially all radiation. The opening between the jaws defines a rectangular opening 22 (FIG. 1b) in which radiation is let through. Within this opening the MLC 18 is used to shape the beam.

Figure 1B:
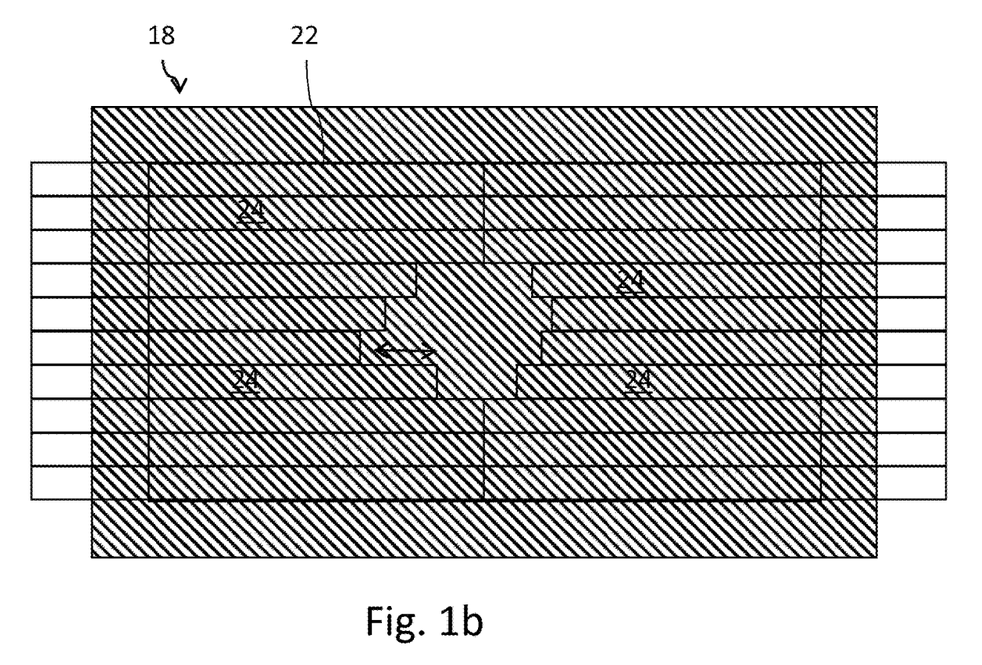

FIG. 1b illustrates the function of the MLC 18 seen in a plane defined by the line A-A in FIG. 1a. The rectangular opening 22 defined by the jaws is shown as a square frame. The MLC 18 has a number of adjacent leaves 24, each of which can be positioned individually to extend into the opening 22, so that together they define an area within the opening 22 in which the radiation from the gantry 12 should be blocked. For clarity only some of the leaves are marked with reference numerals. The positions of the end points of the leaves are referred to as MLC opening or leaf positions, and are specified in each control point (or segment) within a beam together with the jaw positions, MU, gantry angle etc. In the portion of the rectangular opening 22 not blocked by the MLC leaves, the therapeutic radiation will be let through to the patient. Creating a treatment plan for a patient includes determining the MLC leaf positions, the jaw positions and the output (MU) of each control point. The plan creation can be performed using several planning techniques such as forward planning or inverse planning, as described above.

Figure 2:
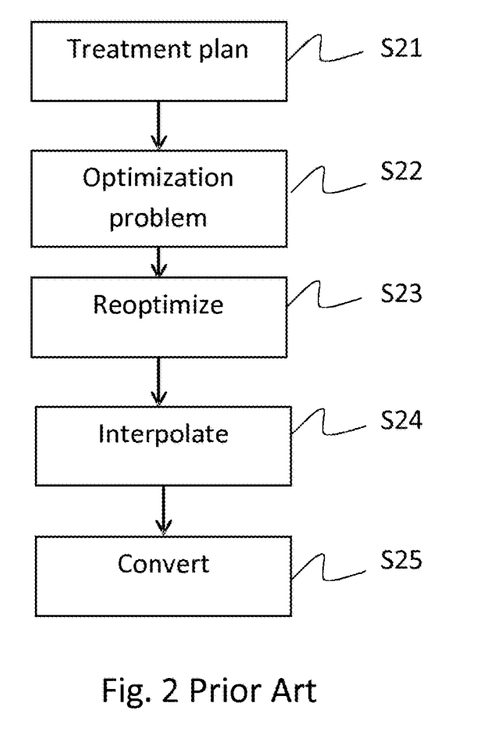
FIG. 2 is a flow chart of a prior art interpolation method.

FIG. 2 is a flow chart of an optimization method according to the prior art. In step S21 an initial treatment plan is obtained, which may be a fluence based treatment plan or a deliverable plan, that is, a treatment plan defining machine settings.

In step S22 a modification is made to the optimization problem, and in step S23 the new treatment plan is obtained by reoptimization of the initial treatment plan. In step S24 fluence interpolation is performed, that interpolation is performed on fluence based parameters, which have a linear relationship to the dose. In step S25 the interpolated fluence based treatment plan is converted to a deliverable plan.

The conversion step S25 introduces deviations from the fluence based plan. If the interpolation in step S24 is instead performed directly in the deliverable plan the conversion step S25 is not needed. Since the machine settings are not linearly related to the dose, differences between the initial treatment plan and the new treatment plan may lead to undesired effects. The prior art solution is that in step S22 only minor modifications may be made to the optimization problem when interpolating between deliverable plans.

Figure 3:
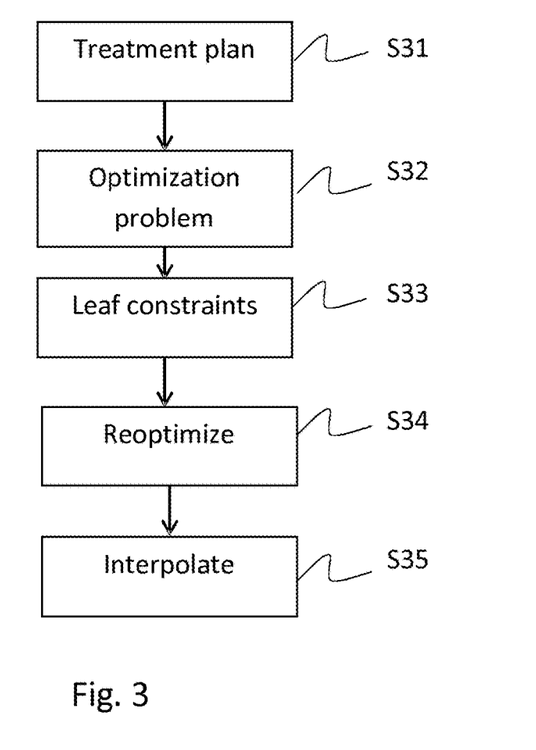
FIG. 3 is a flow chart of an interpolation method according to a first embodiment of the invention.

FIG. 3 is a flow chart of a method according to a first embodiment of the invention. In step S31 a first deliverable treatment plan is obtained in any suitable way available to the skilled person.

In step S32 an optimization problem is defined, focusing on improving one or more aspects of the dose distribution. This can be done by automatically defining objectives or constraints to maintain some qualities of the dose distribution and adding objectives to improve other aspects of the dose distribution, or if the first plan was optimized the first optimization problem can be modified into a second optimization problem, or by defining any new optimization problem. For example, the aim may be to reduce the dose to one or more organs at risk while maintaining target coverage. In step S33 a set of bounds on the leaf positions for the leaves of the MLC are defined. The bounds limit how much each leaf is allowed to move during optimization, from its position in the original deliverable treatment plan to the new position in the optimized treatment plan. The order of steps S32 and S33 is arbitrary.

In step S34, reoptimization of the initial deliverable treatment plan is performed, starting from the beam settings of the first deliverable plan, to improve the plan with respect to the second optimization problem while conforming to the set of bounds on the leaf positions for the leaves of the MLC. In this setting it is not necessary to set boundaries for the dose. Instead, the dose is allowed to vary as much as necessary to improve the new objectives. Reoptimization in this case does not involve replacing the initial plan. Instead, the initial plan is also kept.

In step S35 an interpolation is performed between the first deliverable treatment plan and the second deliverable treatment plan. In one embodiment linear interpolation of the control points is used but other interpolation methods may be used as well. The interpolation may be made using equal weights for the two plans, or may be weighted in favour of one or the other plan. Of course, a number of interpolations using different weights may be performed and the most favourable one may be selected. In a preferred embodiment the computer program controlling interpolation is set up to enable seamless navigation between the two deliverable treatment plans. In this way the operator can select in near-real time the preferred weight between the two treatment plans, which will result in the best possible interpolated treatment plan.

Figure 4:
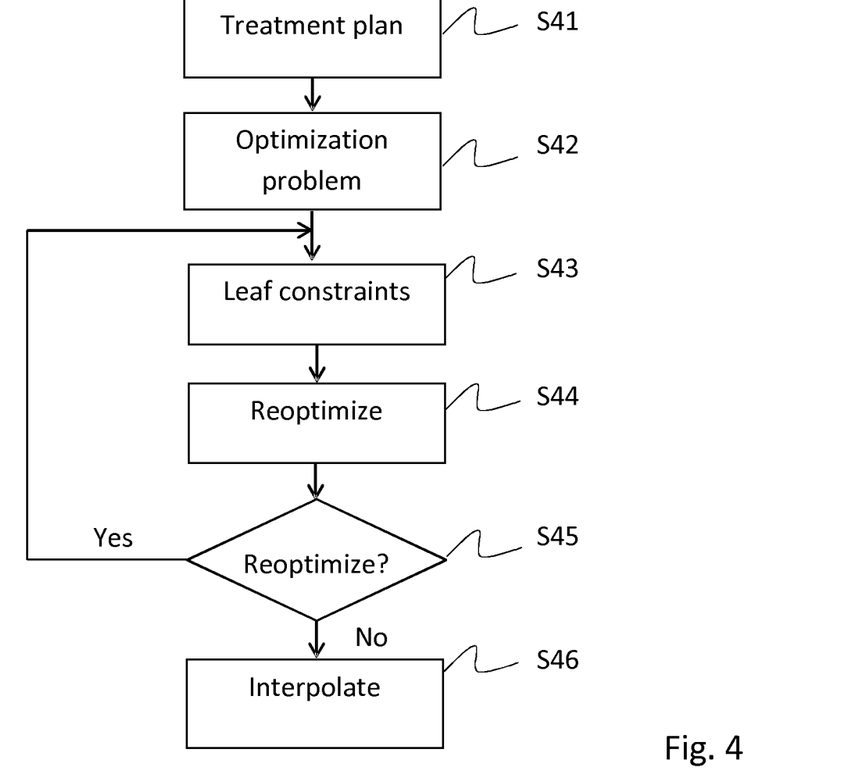
FIG. 4 is a flow chart of an interpolation method according to a second embodiment of the invention.

An alternative embodiment is shown in FIG. 4, in which a greater total movement of the leaves than the maximum distance bound may be allowed by performing a sequence of reoptimizations based on the same optimization problem but allowing the leaves to move only up to the maximum distance bound for each reoptimization. As in FIG. 3, the method starts in step S41 with obtaining a first deliverable treatment plan. Then in step S42, corresponding to step S32 above, an optimization problem is defined. In step S43, a limit is set for the maximal movement of the leaves of the MLC between the first plan and the second plan. In step S44 reoptimization of the first deliverable treatment plan is performed based on the optimization problem in step S42 and the leaf constraints set in step S43, resulting in a second deliverable plan. As in the other embodiments, the initial plan is also kept. Step S45 is a decision step for deciding if another optimization should be carried out. The decision step could include analysing the plan quality improvement between the two last optimizations and continue the optimization if the plan quality improvement is still significant. It could also include performing a maximum number of reoptimizations. If the answer is yes, the procedure reverts to step S43 in which new leaf constraints may be set based on the leaf positions of the second plan. Step S44 is then performed again, reoptimizing the second deliverable treatment plan, using the same optimization problem as for the second plan and different leaf constraints. If the answer in step S45 is no, the procedure continues with step S46, in which a virtual interpolation between the first and the last created treatment plan is performed using the intermediate plans. Each interpolation is in reality performed between either the first and the second treatment plans, the second and the third treatment plans, the third and the fourth treatment plans, and similarly for any further treatment plans produced by subsequent reiterations of the decision loop comprising S45, S43 and S44.

It should be noted that the order or steps S42 and S43 is arbitrary, but the optimization problem is normally not changed.

In each of the iterations of the loop, step S44 may also comprise performing a sequence of optimization steps where both the optimization problem is modified and the leaf position bounds are updated between all reoptimizations.

Figure 5:
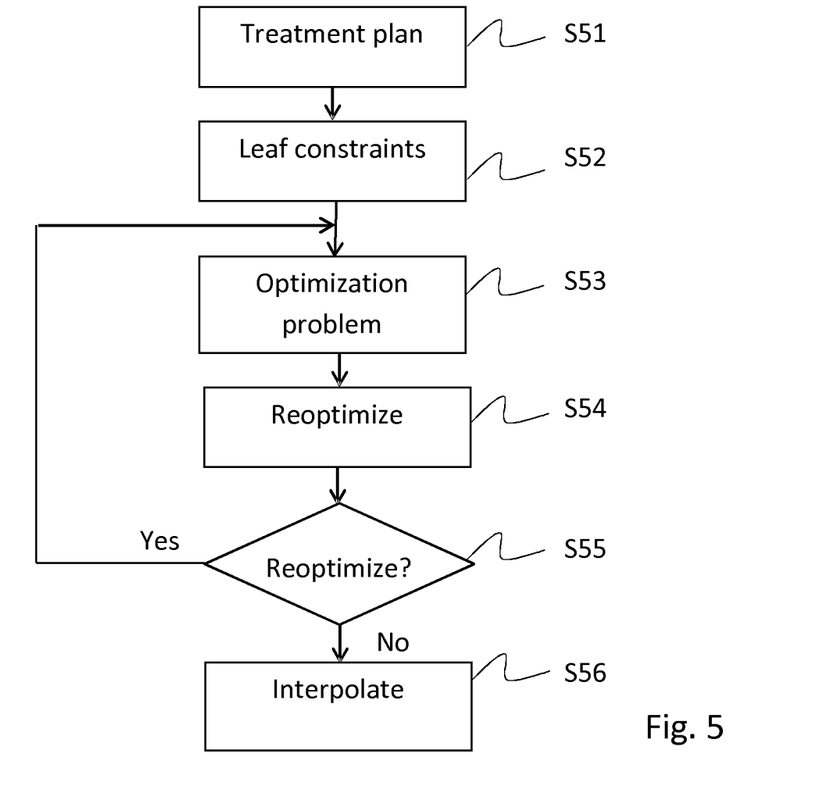
FIG. 5 is a flow chart of an interpolation method according to a third embodiment of the invention.

FIG. 5 illustrates a third embodiment of the invention. Step S51 is the same as steps S31 and S41. In step S52 leaf position bounds are defined and the same bounds are applied for all coming optimizations. In step S53 a second optimization problem is defined. In step S54 the first treatment plan is reoptimized using the optimization problem in step S53 and the leaf constraints set in step S52, resulting in a second deliverable plan. Step S55 is a decision step for deciding if another optimization should be performed. If the answer is yes, the procedure reverts to step S53 in which a new optimization problem may be defined. Then the first treatment plan is reoptimized again based on the leaf constraints set in step S52 and the new optimization problem. If the answer in step S55 is no, the procedure continues with step S56, in which interpolation is performed between two or more of the first and the second deliverable treatment plan and any further treatment plans produced by subsequent reiterations of the decision loop comprising S55, S53 and S54. Since all optimized plans are within the leaf bounds of the initial plan it is possible to interpolate between all deliverable plans. All the optimization problems would preferably be specified in advance before the optimization has started, and the decision step reduces to reoptimize if not all optimization problems have been optimized. This method could be used for generating Pareto plans for a multi-criteria optimization (MCO) navigation tool where the Pareto surface is navigated.

Figure 6:
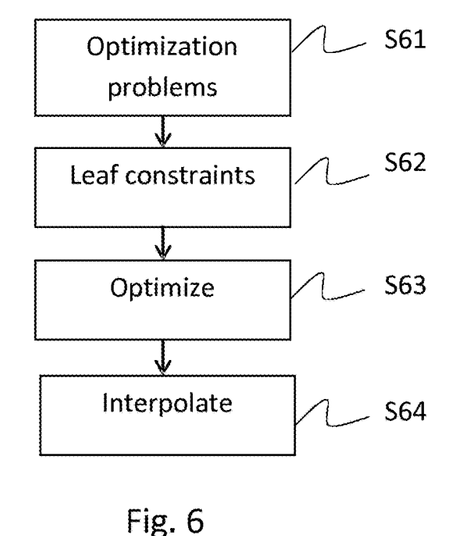
FIG. 6 is a flow chart of an interpolation method according to a fourth embodiment of the invention.

FIG. 6 is a flow chart of a fourth embodiment of the invention, in which two or more deliverable treatment plans are obtained based on different optimization problems. Thus is in contrast to the embodiments of FIGS. 3-5, in which each optimized treatment plan was based on a previous one, FIG. 6 optimizes all treatment plans simultaneously. In step S61 a number of optimization problems are defined. Each optimization problem will serve as basis for a deliverable treatment plan. The optimization problems may be based on the same clinical goals but prioritizing them differently. In step S62 leaf constraints are defined to set a limit to how much leaf positions may differ between the deliverable plans that are to be calculated based on the optimization problems. In step S63 all deliverable treatment plans are optimized based on their respective optimization problems and applying the leaf constraints to ensure that the control points do not differ too much between all combinations of the deliverable treatment plans. In step S64 deliverable plan interpolation is performed between two or more of the deliverable treatment plans obtained in step S63. This method could be used for generating Pareto plans for a multi-ctriteria optimization (MCO) navigation tool where the Pareto surface is navigated.

Figure 7:
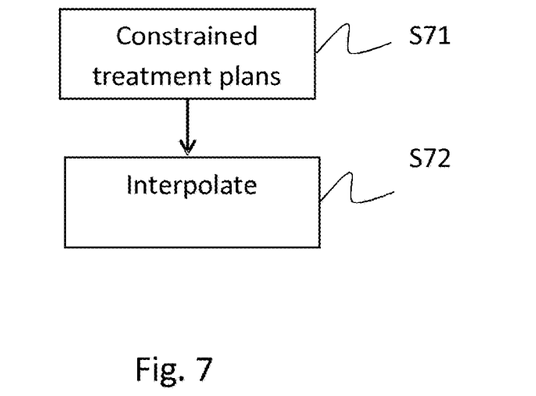
FIG. 7 is a flow chart of an overall interpolation method according to the invention.

FIG. 7 illustrates a general form of the inventive method. In step S71 a number of deliverable treatment plans are obtained. The treatment plans are obtained in such a way as to ensure that they fulfil leaf constraints preventing the MLC leaf positions from differing too much between the treatment plans. In step S72 interpolation is performed between the deliverable treatment plans. The plans can be created using any planning technique, as long as the leaf and/or jaw position constraints are fulfilled.

In each of the flow charts above, interpolation may be performed between two or more deliverable treatment plans. Preferably, interpolation is weighted, to enable a more flexible combination of the treatment plans.

To increase the speed of the navigation and to enable a real time feeling of the navigation it is possible to interpolate the dose instead of the control points during navigation, i.e. when the slider is moved. This is possible since, when constraining leaf positions, the dose distribution computed from the interpolated control points is approximately the same as the dose distribution obtained from interpolating the dose distributions. Only when the slider is released the actual control points are interpolated and the deliverable dose is computed and displayed.

Figure 8:
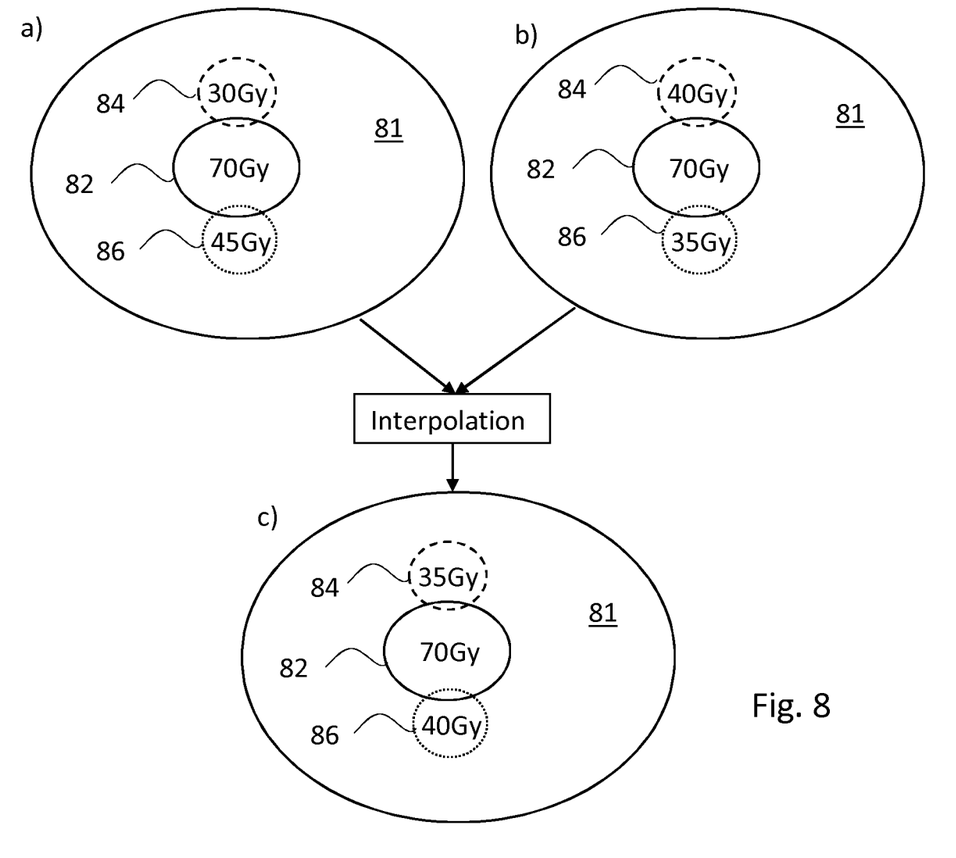
FIG. 8 illustrates schematically interpolation between two plans in a prostate patient.

FIG. 8 shows schematically three different treatment plans for a prostate patient. The two uppermost treatment plans a) and b) and an interpolated plan c). The uppermost treatment plans a) and b) are created according to one of the methods above, that is, with constraints on the maximum difference in MLC leaf positions between them. Each of the treatment plans a), b) and c) is shown on a slice 81 of the patient's body. The target area 82, in this case the prostate, is found centrally in the section. Two organs at risk have been segmented: the urinary bladder 84 and the rectum 86, which partially overlap with the target area. The two uppermost treatment plans a) and b) may be initial treatment plan that has been optimized using a traditional set of objectives and an optimized treatment plan that has been optimized from the initial treatment plan to reduce the dose to the rectum. As can be seen, the dose to the target area 82 is the same, 70 Gy in both a) and b). The dose to the rectum 86 has been reduced from 45 Gy in a) to 35 Gy in b), but with the undesired effect of increasing the dose to the bladder 84 from 30 Gy to 40 Gy.

It would be advantageous if the dose to the bladder could be lower than it is in b) while the dose to the rectum should be kept as close to the value in b) as possible. The dose to the target organ 82 should not go below 70 Gy. One way of achieving this is to interpolate between the two plans marked as a) and b) to create an interpolated plan c). Different weights may be assigned to the plans included in the interpolation, which will result in different interpolation results. Therefore, it is possible to vary the weights and select the best possible interpolation result as a starting point for treatment. In the example shown in FIG. 8, the best result is the one denoted c). The dose to the target area is still 70 Gy, and the doses to the rectum 86 and bladder 84 are 40 Gy and 35 Gy, respectively, which means they both get an intermediate dose between the dose in a) and the dose in b).

Because of the leaf position constraints used when creating the two first plans a) and b), it is possible to interpolate in deliverable plans without losing target coverage, because the interpolation of the deliverable beam setups give approximately the same dose distribution as a direct interpolation of the two dose distributions.

Figure 9:
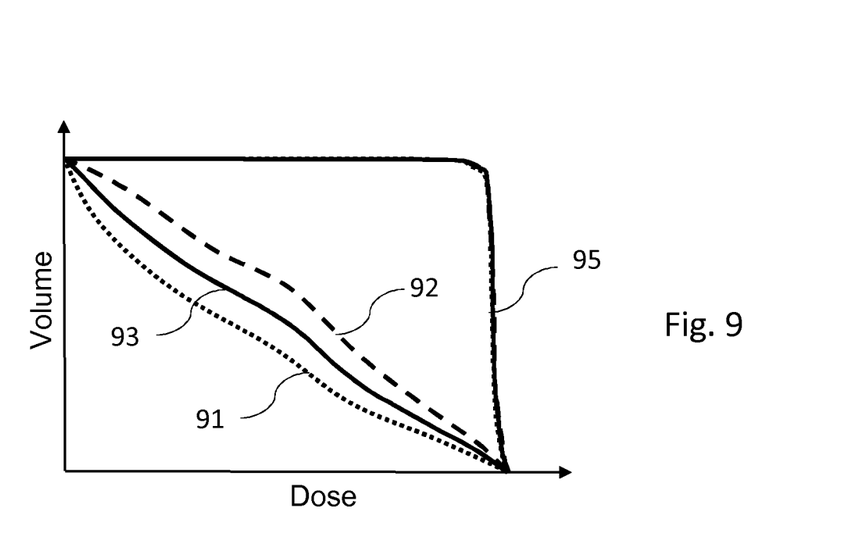
FIG. 9 is a first example of a resulting dose distribution of interpolation between two treatment plans according to the invention.

An example of dose distribution in the target and in an organ at risk is shown in FIG. 9, which is a cumulative dose-volume histogram DVH showing the dose along the X-axis and the volume of the respective organ, as a percentage of the organ's total volume, along the Y-axis. The dose distributions for a first deliverable treatment plan, a second deliverable treatment plan and a third deliverable treatment plan, which is the result of interpolation between the first and the second plan, are shown. The first and second plans were obtained according to one of the flow charts of FIGS. 3-7, that is, with limits to change in the leaf positions between the first and the second plan.

A dotted curve 91 and a dashed curve 92 indicate the dose to the organ at risk in the first plan and in the second plan, respectively. A solid line 93 between the dotted curve 91 and the dashed curve 92 is the dose distribution according to the interpolated plan. A somewhat blurred curve 95 is actually three curves on top of each other: a dashed curve, a dotted curve and a solid curve, representing the dose to the target organ according to the first, the second and the interpolated treatment plan, respectively. As can be seen, the three curves overlap nearly perfectly ensuring a uniform dose in the target.

Figure 10:
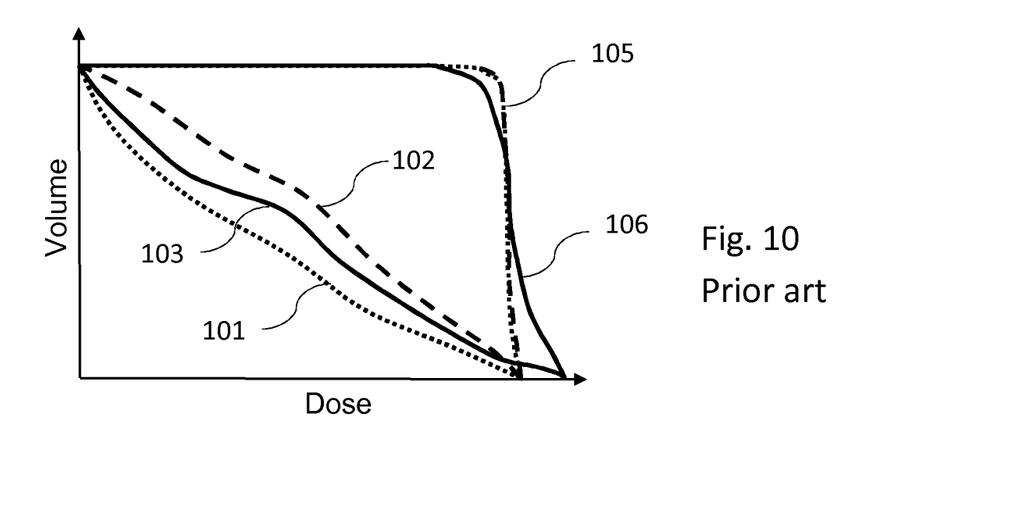
FIG. 10 is a second example of a resulting dose distribution interpolation between two treatment plans shown when the inventive method is not applied.

FIG. 10 shows an example of DVH showing the dose distribution in the target and in an organ at risk for a first deliverable treatment plan, a second deliverable treatment plan and a third deliverable treatment plan, which is the result of interpolation between the first and the second plan, are shown. In this example, no constraint regarding leaf positions was applied to the first or second plan.

A dotted curve 101 and a dashed curve 102 indicate the dose to the rectum in the first plan and in the second plan, respectively. A solid line 103 between the dotted curve 101 and the dashed curve 102 is the dose distribution according to the interpolated plan. As can be seen from the solid curve, a portion of the organ at risk will receive an unacceptably high dose. The curves representing the dose to target are more different in this case. The dashed and the dotted lines corresponding to the first and the second plan practically overlap and are denoted 105. A solid line 106 representing the target dose according to the interpolated treatment plan has some undesired effects in that the target dose will be non-uniform over the target volume and in particular that part of the target will receive a too low dose.

Ideally an interpolation tool is developed which will enable the operator to navigate seamlessly between all of the deliverable plans from the initial plan used in the first loop to the last optimized plan to see the resulting dose distribution from each of the optimized plans and also the possible results of interpolating between them. Preferably the result should be displayed in the form of DVHs and/or 3D dose distribution, in which the curves and/or the dose distribution will change as a result of sliding an interpolation handle between positions representative of the different deliverable treatment plans. It should be recalled that the interpolation may be performed between two adjacent plans, using weights for each of the plans. Such tools are available for other interpolation functions and would be fairly straight-forward to modify for use with the invention.

An advantageous application of the invention would be to create a number of plans, where each plan focus on one or more objectives with different priorities on the objectives. In one setting these plans could be used to span the so called pareto surface. These plans can then be navigated using interpolation between two or more of the plans, to find the best trade-off between the different goals. In these situations it is often beneficial to drive the optimization as far as possible in the direction of the highly prioritized objectives. It is thus not enough to make a minor modification to the dose distribution.

Figure 11:
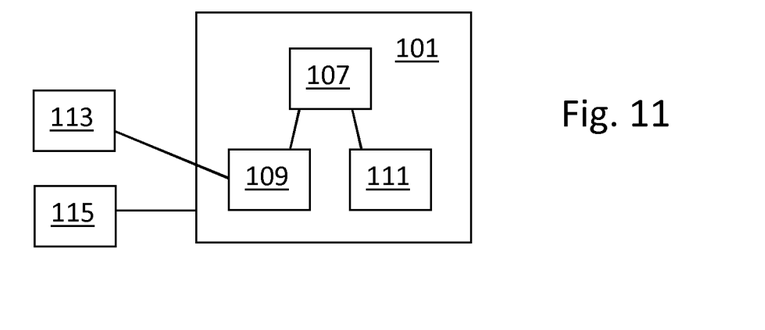
FIG. 11 is a computer system for performing an optimization according to an embodiment of the invention.

FIG. 11 illustrates a computer system for performing the optimization according to the invention. A computer 101 is arranged to optimize a radiotherapy treatment plan to create an optimized treatment plan based on the initial radiotherapy treatment plan. The computer 101 may be the same processor as the one used to determine the initial radiotherapy treatment plan according to algorithms well known in the art, or the initial plan may be provided in some other way. For performing the updating, the computer 101 comprises processing means 107 which will be discussed in more detail below. The computer 101 also comprises data memory 109 and program memory 111. The data memory 109 is arranged to hold the following for use by the processor 107: the created treatment plans, the interpolated treatment plan, and optionally the initial treatment plan. Typically, data input means 113 and user input means 115 as well as other input/output means (not shown) are present. These input/output means may be of any type known in the art.

The program memory 111 is arranged to hold the computer program for optimizing the deliverable treatment plan in accordance with one or more of the methods discussed in connection with FIGS. 6, 9 and 10. When run, the computer program will control the processor to perform the interpolation process based on the deliverable treatment plans.

The invention claimed is:

1. A method of creating an interpolated radiotherapy treatment plan for delivering a radiation beam from a radiotherapy system comprising at least one of jaws and a multi-leaf collimator with leaves for shaping the radiation beam, the method comprising the following steps:
   providing a first deliverable treatment plan comprising at least one of the following:
      first leaf position settings for a number of leaves of the multi-leaf collimator; and
      first jaw position settings for the jaws;
   providing a second deliverable treatment plan comprising at least one of the following:

second leaf position settings for a number of leaves of the multi-leaf collimator; and second jaw position settings for the jaws;

wherein the second deliverable treatment plan is obtained using at least one of the following constraints:

a maximum difference in position settings for each leaf between the first and second leaf position settings of the first and second deliverable treatment plans, a maximum difference in positions of the jaws between the first and the second jaw position settings of the first and second deliverable treatment plans; and creating an interpolated treatment plan based on the first and the second deliverable treatment plans, wherein the interpolated treatment plan controls the radiotherapy system to deliver the radiation beam, and wherein a treatment plan is deliverable at least when the treatment plan satisfies a predefined objective and no conversion step is required for the treatment plan to be delivered on the radiotherapy system.

2. The method according to claim 1, wherein the second deliverable treatment plan is created based on the first deliverable treatment plan.

3. The method according to claim 2, comprising the step of:

obtaining an additional deliverable treatment plan based on the first deliverable treatment plan, the additional deliverable treatment plan comprising at least one of the following:

additional leaf position settings for a number of leaves of the multi-leaf collimator; and additional jaw position settings for the jaws;

optimizing the additional deliverable treatment plan using an additional optimization problem; and applying at least one of the following constraints:

a maximum difference in leaf positions between the first and the additional leaf position settings of the first and additional deliverable treatment plans;

a maximum difference in positions of the jaws between the first and the additional jaw position settings of the first and additional deliverable treatment plans; and obtaining the interpolated treatment plan based on an interpolation between either the first and the second deliverable treatment plan, or between the first and the additional deliverable treatment plan, or the second and the additional deliverable treatment plan, or the first and the second and the additional deliverable treatment plan.

4. The method according to claim 1, wherein the first deliverable treatment plan and the second deliverable treatment plan are optimized simultaneously using a first and a second optimization problem, respectively.

5. The method according to claim 4, comprising the step of:

providing a third deliverable treatment plan comprising at least one of the following:

third leaf position settings for a number of leaves of the multi-leaf collimator; and third jaw position settings for the jaws;

wherein the third deliverable treatment plan is obtained using at least one of the following constraints:

a maximum difference in leaf positions between the first, the second, and the third leaf position settings of the first, second, and third deliverable treatment plans and any further treatment plan, a maximum difference in positions of the jaws between the first, the second, and the third jaw position settings of the first, second, and third deliverable treatment plans and any further treatment plan, optimizing the third deliverable treatment plan using a third optimization problem simultaneously with optimizing the first and second deliverable treatment plans, and obtaining the interpolated treatment plan based on at least two of the deliverable treatment plans.

6. The method according to claim 4, comprising the steps of:

providing an additional deliverable treatment plan based on the second deliverable treatment plan, the additional deliverable treatment plan comprising at least one of the following:

additional leaf position settings for a number of leaves of the multi-leaf collimator; and additional jaw position settings for the jaws;

optimizing the additional deliverable treatment plan using an additional optimization problem and applying at least one of the following constraints:

a maximum difference in leaf positions between the second and the additional leaf position settings of the second and the additional deliverable treatment plans;

a maximum difference in positions of the jaws between the second and the additional jaw position settings of the second and the additional deliverable treatment plans; and obtaining the interpolated treatment plan based on interpolation of the first and the second deliverable treatment plan, or the second and the additional deliverable treatment plan.

7. The method according to claim 6, wherein the additional optimization problem is identical to the second optimization problem.

8. The method according to claim 1, wherein the maximum difference in position settings for each leaf substantially corresponds to a fluence resolution.

9. The method according to claim 1, wherein the maximum difference in position settings for each leaf is set between 0.01 cm and 2 cm.

10. The method according to claim 9, wherein the maximum difference in position settings for each leaf is set between 0.5 cm and 1.5 cm.

11. A computer program product, stored on a carrier, comprising a non-transitory computer readable medium which, when run in a computer, will cause the computer to perform the method according to claim 1.

12. A computer system for performing dose calculations for radiotherapy, the system comprising a processor for performing registration of images, said computer system having a memory having stored therein the computer program product according to claim 11 in such a way that the computer program product, when executed, will control the processor.

* * * * *